United States Patent [19]
Chen et al.

[11] Patent Number: 6,166,274
[45] Date of Patent: Dec. 26, 2000

[54] CATALYZED LIQUID PHASE FLUORINATION OF 1230ZA

[75] Inventors: Bin Chen, Treddyfrin; Michael S. Bolmer, Lower Providence; Maher Y. Elsheikh, Tredyffrin, all of Pa.

[73] Assignee: ATOFINA Chemicals, Inc., Philadelphia, Pa.

[21] Appl. No.: 09/461,587

[22] Filed: Dec. 15, 1999

[51] Int. Cl.$^7$ .................................................. C07C 17/20
[52] U.S. Cl. ............................................................ 570/160
[58] Field of Search ................................................ 570/160

[56] References Cited

U.S. PATENT DOCUMENTS

| | | | |
|---|---|---|---|
| 5,214,223 | 5/1993 | Eicher et al. | 570/166 |
| 5,616,819 | 4/1997 | Boyce et al. | 570/167 |
| 5,811,603 | 9/1998 | Elsheikh | 570/166 |
| 5,877,359 | 3/1999 | Elsheikh | 570/160 |

*Primary Examiner*—Alan Siegel

[57] ABSTRACT

A liquid phase process is provided for the preparation of 1233zd with reduced oligomer formation via the fluorination of 1230za with HF in the presence of a catalyst selected from TFA and triflic acid. The 1233zd is a known intermediate useful for preparing 245fa.

3 Claims, No Drawings

CATALYZED LIQUID PHASE FLUORINATION OF 1230ZA

BACKGROUND OF THE INVENTION

This invention relates to preparation of 1,1,1-trifluoro-3-chloro-2-propene (1233zd) with reduced oligomer formation ("reduced oligomer formation" referring to less than about 3 weight % oligomer formation) by the catalyzed liquid phase fluorination of 1,1,3,3-tetrachloro-2-propene (1230za) wherein 1230za is contacted with hydrogen fluoride ("HF") in the presence of a catalyst selected from trifluoroacetic acid ("TFA") or trifluoromethanesulfonic acid ("triflic acid"). The 1233zd product is a known intermediate for producing 245fa, as taught, for example, in U.S. Pat. Nos. 5,616,819 and 5,895,825.

U.S. Pat. No. 5,616,819 discloses that previous attempts to fluorinate 1230za to 1233zd in a catalyzed liquid phase reaction resulted in the formation of a reaction mixture contacting primarily oligomeric products.

U.S. Pat. No. 5,877,359 discloses an uncatalyzed liquid process for fluorinating 1230za to 1233za with reduced oligomer formation, but such a process requires high HF:1230za molar ratios and the use of high temperatures and/or long reaction times.

It is thus an object of this invention to provide a catalyzed process for producing 1233zd with reduced oligomer formation.

BRIEF SUMMARY OF THE INVENTION

A catalyzed liquid phase process for preparing 1233zd is provided, which process comprises contacting 1230za with HF in the presence of a catalyst selected from triflic acid or, preferably, TFA under conditions sufficient to produce 1233zd with less than about 3 weight % oligomer formation. The major by-product of the reaction, hydrogen chloride (HCl), is then separated from the resulting reaction mixture by conventional means known in the art (such as absorption or distillation). Further purification of the resulting product is not necessary if it is intended to be used to produce 245fa.

DETAILED DESCRIPTION

It has now been discovered that the use of triflic acid or TFA as the catalyst in a liquid phase process for fluorination of 1230za with HF enables one to produce 1233zd with less than about 3 weight % oligomer formation and, under optimum conditions, with less than about 1 weight % oligomer formation.

Preparation of the 1230za starting material is taught, for example, in U.S. Pat. No. 5,689,020.

The process of this invention may be conducted as a batch or continuous process. The HF:1230za molar ratio is typically from at least about 3:1 to about 200:1, but is preferably from about 6:1 to about 200:1. The catalyst: 1230za molar ratio is typically from about 0.001 to about 0.1, preferably from about 0.01 to about 0.05. Temperatures of from about 20° C. to about 200° C. are typically used, preferably from about 50° C. to about 120° C. Pressures are typically from about 0 to about 800 psig, preferably from about 35 to about 500 psig. Residence time is normally from about 5 minutes to 5 hours, preferably from about ½ to about 2 hours. HCl, the principal by-product, may be removed from the resultant reaction mixture by methods known in the art such as by absorption (in water or caustic solution) or distillation. The remaining liquid, composed primarily of 1233zd with some HF, can be used without further purification for production of 245fa by methods known to the art.

The practice of the invention is illustrated in more detail in the following non-limiting examples. Varying mole ratios of 1230za and HF were gradually heated with stirring for about one hour in the presence of varying amounts of catalyst, under the conditions, and with the results shown in the following table. HCl and HF were removed from the resulting mixture by washing with water scrubber solution.

| Example # | 1 | 2 | 3 | 4 |
|---|---|---|---|---|
| Temperature (° C.) | 50 | 80 | 50 | 50 |
| Pressure (psig) | 400 | 400 | 400 | 400 |
| HF:1230za (m.r.) | 160 | 6 | 148 | 150 |
| TFA:1230za (m.r.) | .05 | .012 | | |
| Triflic Acid: 1230za (m.r.) | | | .027 | .05 |
| Conversion of 1230za (%) | 100 | 93 | 99 | 100 |
| Selectivity for 1233zd (%) | 87 | 95 | 56 | 76 |
| Oligomer formation (%) | 1.1 | 0.4 | 2.5 | 0.5 |

We claim:

1. A process for preparing 1,1,1-trifluoro-3-chloro-2-propene comprising contacting 1,1,3,3-tetrachloro-2-propene with hydrogen fluoride in the liquid phase in the presence of a catalyst selected from the group consisting of trifluoromethanesulfonic acid and trifluoroacetic acid under conditions sufficient to produce 1,1,1-trifluoro-3-chloro-2-propene with less than about 3% oligomer formation.

2. A process for preparing 1,1,1-trifluoro-3-chloro-2-propene comprising contacting 1,1,3,3-tetrachloro-2-propene with hydrogen fluoride in the liquid phase in the presence of trifluoromethanesulfonic acid under conditions sufficient to produce 1,1,1-trifluoro-3-chloro-2-propene with less than about 3% oligomer formation.

3. A process for preparing 1,1,1-trifluoro-3-chloro-2-propene comprising contacting 1,1,3,3-tetrachloro-2-propene with hydrogen fluoride in the liquid phase in the presence of trifluoroacetic acid under conditions sufficient to produce 1,1,1-trifluoro-3-chloro-2-propene with less than about 3% oligomer formation.

* * * * *